US00PP19102P2

(12) United States Plant Patent
Rendle

(10) Patent No.: US PP19,102 P2
(45) Date of Patent: Aug. 12, 2008

(54) CORDYLINE PLANT NAMED 'SOUTHERN SPLENDOUR'

(50) Latin Name: *Cordyline australis*
Varietal Denomination: Southern Splendour

(75) Inventor: Arthur George Rendle, Auckland (NZ)

(73) Assignee: Plant Marketing International Ltd., Sussex (GB)

( * ) Notice: Subject to any disclaimer, the term of this patent is extended or adjusted under 35 U.S.C. 154(b) by 0 days.

(21) Appl. No.: 11/728,153

(22) Filed: Mar. 23, 2007

(51) Int. Cl.
*A01H 5/00* (2006.01)

(52) U.S. Cl. ..... Plt./383
(58) Field of Classification Search ..... Plt./383
See application file for complete search history.

*Primary Examiner*—Annette H Para
(74) *Attorney, Agent, or Firm*—C. A. Whealy

(57) ABSTRACT

A new and distinct cultivar of *Cordyline* plant named 'Southern Splendour', characterized by its upright and outwardly arching growth habit; slender stems with short internodes; long arching linear leaves with pink and brown-colored longitudinal stripes; and good keeping quality and garden performance.

1 Drawing Sheet

Botanical designation: *Cordyline australis.*
Cultivar denomination: 'Southern Splendour'.

BACKGROUND OF THE INVENTION

The present invention relates to a new and distinct cultivar of *Cordyline* plant, botanically known as *Cordyline australis,* and hereinafter referred to by the name 'Southern Splendour'.

The new *Cordyline* is a naturally-occurring whole plant mutation of the *Cordyline australis* cultivar Red Star, not patented. The new *Cordyline* was discovered and selected by the Inventor within a population of plants of the parent selection in a controlled environment in Newmarket, Auckland, New Zealand in 1996.

Asexual reproduction of the new *Cordyline* by micropropagated cuttings in Newmarket, Auckland, New Zealand since 1997, has shown that the unique features of this new *Cordyline* are stable and reproduced true to type in successive generations.

SUMMARY OF THE INVENTION

The cultivar Southern Splendour has not been observed under all possible environmental conditions. The phenotype may vary somewhat with variations in environment such as temperature and light intensity, without, however, any variance in genotype.

The following traits have been repeatedly observed and are determined to be the unique characteristics of 'Southern Splendour'. These characteristics in combination distinguish 'Southern Splendour' as a new and distinct cultivar of *Cordyline:*

1. Upright and outwardly arching growth habit.
2. Slender stems with short internodes.
3. Long arching linear leaves with pink and brown-colored longitudinal stripes.
4. Good keeping quality and garden performance.

Plants of the new *Cordyline* differ from plants of the parent, the cultivar Red Star, primarily in foliage color as plants of the cultivar Red Star have dark burgundy red-colored leaves.

Plants of the new *Cordyline* can be compared to plants of the *Cordyline australis* cultivar Torbay Dazzler, not patented. Plants of the new *Cordyline* differ primarily from plants of the cultivar Torbay Dazzler in foliage color as plants of the cultivar Torbay Dazzler have green and creamy white-colored leaves.

BRIEF DESCRIPTION OF THE PHOTOGRAPHS

The accompanying photographs illustrate the overall appearance of the new *Cordyline.* This photographs show the colors as true as it is reasonably possible to obtain in colored reproductions of this type. Colors in the photographs may differ slightly from the color values cited in the detailed botanical description which accurately describe the colors of the new *Cordyline.*

The photograph at the top of the sheet comprises a side perspective view of a typical two-year old plant of 'Southern Splendour' grown in a container.

The photograph at the bottom of the sheet is a close-up view of the upper surface of a typical leaf of 'Southern Splendour'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Las Pallas, Murcia, Spain during the spring and early summer in a polyethylene-covered greenhouse and under conditions and practices which approximate those generally used in commercial *Cordyline* production. During the production of the plants, day temperatures ranged from 25° C. to 30° C. and night temperatures ranged from 16° C. to 22° C. Plants were about two years old when the photographs and the botanical description were taken.

Botanical classification: *Cordyline australis* cultivar Southern Splendour.

Parentage: Naturally-occurring whole plant mutation of the *Cordyline australis* cultivar Red Star, not patented.

Propagation:

*Type.*—By micropropagated cuttings.

*Time to initiate roots.*—About two weeks at 22° C.

*Time to produce a rooted young plant.*—About 56 to 60 days at 22° C.

*Root description.*—Medium thickness, fibrous; white in color.

*Rooting habit.*—Moderately branching; sparse.

Plant description:

*Plant form/growth habit.*—Upright and outwardly arching plant habit; broadly inverted triangle with arching leaves. Moderately vigorous growth habit.

*Plant height.*—About 100 cm.

*Plant diameter or spread.*—About 50 cm.

Stem description:

*Diameter, at base.*—About 2.5 cm; slender.

*Internode length.*—About 1 cm.

*Color.*—Close to 187A.

*Texture.*—Smooth, glabrous.

Foliage description:

*Orientation.*—Initially erect to outwardly arching.

*Arrangement.*—Whorled; sessile.

*Shape.*—Linear.

*Apex.*—Acute.

*Margin.*—Entire.

*Texture, upper and lower surfaces.*—Leathery; smooth, glabrous.

*Luster, upper surface.*—Glossy.

*Luster, lower surface.*—Dull.

*Venation pattern.*—Parallel.

*Length.*—About 60 cm to 70 cm.

*Width.*—About 1.5 cm to 3 cm.

*Color.*—Developing and fully expanded leaves, upper surface: Alternating longitudinal stripes of 54A and between 199A and 200A. Developing and fully expanded leaves, lower surface: Alternating longitudinal stripes of 54A and between 199A and 200A. Venation, upper and lower surfaces: Similar to lamina.

Flower description: Plants of the new *Cordyline* do not typically develop flowers.

Disease/pest resistance: Plants of the new *Cordyline* have not been shown to be resistant to pathogens and pests common to *Cordyline*.

Keeping quality: Plants of the new *Cordyline* are durable and will maintain good leaf substance indefinitely under interior conditions.

Garden performance: Plants of the new *Cordyline* have been observed to have good garden performance and tolerate wind, rain and temperatures ranging from about −5° C. to about 35° C.

It is claimed:

1. A new and distinct *Cordyline* plant named 'Southern Splendour' as illustrated and described.

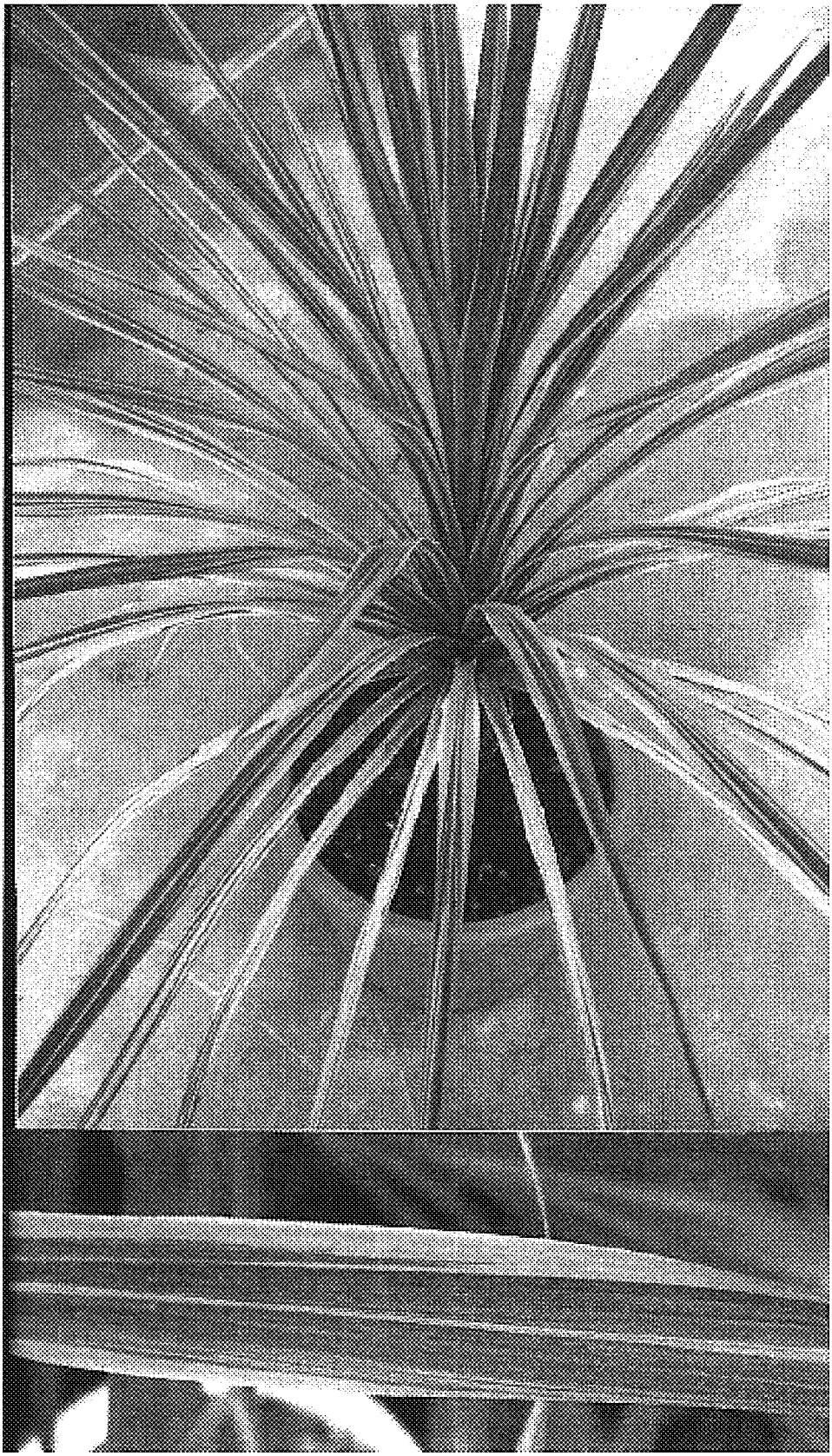

* * * * *